(12) United States Patent
Lacey et al.

(10) Patent No.: US 8,778,669 B2
(45) Date of Patent: Jul. 15, 2014

(54) MULTILAYER TISSUE CULTURE VESSEL (75) Inventors: William J. Lacey, North Andover, MA (US); Michael S. Shanler, Sudbury, MA (US); Amy W. Cai, Brighton, MA (US)

(73) Assignee: Corning Incorporated, Corning, NY (US)

( * ) Notice: Subject to any disclaimer, the term of this patent is extended or adjusted under 35 U.S.C. 154(b) by 530 days.

(21) Appl. No.: 12/840,758

(22) Filed: Jul. 21, 2010

(65) Prior Publication Data

US 2011/0020923 A1    Jan. 27, 2011

Related U.S. Application Data (60) Provisional application No. 61/227,615, filed on Jul. 22, 2009.

(51) Int. Cl.
*C12M 1/00* (2006.01)
*C12M 3/00* (2006.01)
*C12M 1/12* (2006.01)
*C12M 1/24* (2006.01)

(52) U.S. Cl.
CPC ............ *C12M 23/34* (2013.01); *C12M 23/28* (2013.01); *C12M 23/40* (2013.01); *C12M 23/44* (2013.01); *C12M 25/14* (2013.01); *C12M 23/04* (2013.01); *C12M 23/08* (2013.01)
USPC .................. 435/305.2; 435/305.1; 435/305.3; 435/305.4; 435/304.1; 435/288.3; 435/288.4; 435/288.1

(58) Field of Classification Search
CPC ...... C12M 23/28; C12M 23/34; C12M 23/40; C12M 23/44; C12M 23/04; C12M 23/08; C12M 25/14
See application file for complete search history.

(56) References Cited

U.S. PATENT DOCUMENTS

| 3,821,087 A | 6/1974 | Knazek et al. |
| 3,948,732 A | 4/1976 | Haddad et al. |
| 3,997,396 A | 12/1976 | Delente |
| 4,172,013 A | 10/1979 | Skoda et al. |

(Continued)

FOREIGN PATENT DOCUMENTS

| DE | 83 09 876 U1 | 12/1983 |
| EP | 1 514 919 A1 | 3/2005 |

(Continued)

*Primary Examiner* — Nathan Bowers
(74) *Attorney, Agent, or Firm* — Hoffmann & Baron, LLP (57) ABSTRACT

The present invention discloses a vessel for culturing cells which includes: a bottom including a base with an upwardly extending wall at least partially bounding the base of the bottom; a top including a base with a downwardly extending wall at least partially bounding the base of the top; a tubular neck with an opening defined therein; and, one or more shelves, wherein, each shelf includes a base with an upwardly extending wall at least partially bounding the base of the shelf. The upwardly extending wall of a first shelf adjoins the downwardly extending wall of the top with the first shelf being located intermediate the bottom and the top. The base of each of the shelves having at least one aperture formed therein. The bottom, the top and the one or more shelves collectively define an enclosed volume for culturing cells. The tubular neck extends from the vessel with the enclosed volume being accessible by the opening in the tubular neck. Advantageously, this vessel provides high volume cell culture in a manner that increases efficiency and reduces the cost of culturing cells.

29 Claims, 13 Drawing Sheets

(56) References Cited

U.S. PATENT DOCUMENTS

| | | |
|---|---|---|
| 4,184,916 A | 1/1980 | Tolbert et al. |
| 4,225,671 A | 9/1980 | Puchinger et al. |
| 4,332,906 A | 6/1982 | Taylor |
| 4,391,912 A | 7/1983 | Yoshida et al. |
| 4,440,853 A | 4/1984 | Michaels et al. |
| 4,537,860 A | 8/1985 | Tolbert et al. |
| 4,647,539 A | 3/1987 | Bach |
| 4,649,114 A | 3/1987 | Miltenburger et al. |
| 4,661,458 A | 4/1987 | Berry et al. |
| 4,720,462 A | 1/1988 | Rosenson |
| 4,722,902 A | 2/1988 | Harm et al. |
| 4,734,373 A | 3/1988 | Bartal |
| 4,748,124 A | 5/1988 | Vogler |
| 4,749,654 A | 6/1988 | Karrer et al. |
| 4,804,628 A | 2/1989 | Cracauer et al. |
| 4,874,707 A | 10/1989 | Bock |
| 4,889,812 A | 12/1989 | Guinn et al. |
| 4,897,359 A | 1/1990 | Oakley et al. |
| 4,948,728 A | 8/1990 | Stephanopoulos et al. |
| 5,002,890 A | 3/1991 | Morrison |
| 5,015,585 A | 5/1991 | Robinson |
| 5,032,524 A | 7/1991 | Buntemeyer et al. |
| 5,064,764 A | 11/1991 | Besnainon et al. |
| 5,081,035 A | 1/1992 | Halberstadt et al. |
| 5,126,269 A | 6/1992 | Fike et al. |
| 5,135,853 A | 8/1992 | Dziewulski et al. |
| 5,149,649 A | 9/1992 | Miyamori et al. |
| 5,188,962 A | 2/1993 | Hasegawa et al. |
| 5,202,254 A | 4/1993 | Amiot et al. |
| 5,240,854 A | 8/1993 | Berry et al. |
| 5,268,298 A | 12/1993 | Fike et al. |
| 5,290,700 A | 3/1994 | Binot et al. |
| 5,310,676 A | 5/1994 | Johansson et al. |
| 5,316,945 A | 5/1994 | Minuth |
| 5,330,908 A | 7/1994 | Spaulding |
| 5,416,022 A | 5/1995 | Amiot |
| 5,437,998 A | 8/1995 | Schwarz et al. |
| 5,449,617 A | 9/1995 | Falkenberg et al. |
| 5,508,174 A | 4/1996 | DelRaso |
| 5,516,691 A | 5/1996 | Gerlach |
| 5,523,235 A | 6/1996 | Barditch et al. |
| 5,576,211 A | 11/1996 | Falkenberg et al. |
| 5,602,028 A | 2/1997 | Minchinton |
| 5,622,857 A | 4/1997 | Goffe |
| 5,627,070 A | 5/1997 | Gruenberg |
| 5,656,494 A | 8/1997 | Kant et al. |
| 5,658,797 A | 8/1997 | Bader |
| 5,665,398 A * | 9/1997 | McCormick ............ 425/117 |
| 5,686,301 A | 11/1997 | Falkenberg et al. |
| 5,702,945 A | 12/1997 | Nagels et al. |
| 5,705,390 A | 1/1998 | Kadouri et al. |
| 5,712,154 A | 1/1998 | Mullon et al. |
| 5,728,577 A | 3/1998 | Kuriyama |
| 5,763,261 A | 6/1998 | Gruenberg |
| 5,955,353 A | 9/1999 | Amiot |
| 5,981,211 A | 11/1999 | Hu et al. |
| 6,107,085 A | 8/2000 | Coughlin et al. |
| 6,127,141 A | 10/2000 | Kopf |
| 6,214,574 B1 | 4/2001 | Kopf |
| 6,228,607 B1 | 5/2001 | Kersten et al. |
| 6,284,531 B1 | 9/2001 | Zhu |
| 6,342,388 B1 | 1/2002 | Van Den Wildenberg |
| 6,403,369 B1 | 6/2002 | Wood |
| 6,453,310 B1 | 9/2002 | Zander |
| 6,455,007 B1 | 9/2002 | Mansky et al. |
| 6,455,310 B1 | 9/2002 | Barbera-Guillem |
| 6,544,788 B2 | 4/2003 | Singh |
| 6,566,126 B2 | 5/2003 | Cadwell |
| 6,569,675 B2 | 5/2003 | Wall et al. |
| 6,593,136 B1 | 7/2003 | Geiss |
| 6,620,614 B1 | 9/2003 | Luth et al. |
| 6,642,019 B1 | 11/2003 | Anderson et al. |
| 6,670,713 B2 | 12/2003 | Gonzalez et al. |
| 6,702,178 B2 | 3/2004 | Bowers et al. |
| 6,794,184 B1 | 9/2004 | Mohr et al. |
| 6,855,542 B2 | 2/2005 | DiMilla et al. |
| 6,878,344 B2 | 4/2005 | Mansky et al. |
| 6,918,738 B2 | 7/2005 | Lafferty et al. |
| 6,933,144 B2 | 8/2005 | Cadwell |
| 6,987,019 B1 | 1/2006 | Rogalsky |
| 7,022,518 B1 | 4/2006 | Feye |
| 7,033,823 B2 | 4/2006 | Chang |
| 7,078,228 B2 | 7/2006 | Lacey et al. |
| 7,144,727 B2 | 12/2006 | Akers et al. |
| 7,179,636 B2 | 2/2007 | Guillot et al. |
| 7,229,820 B2 | 6/2007 | Wilson |
| 7,425,440 B2 | 9/2008 | Malinge et al. |
| 7,745,209 B2 | 6/2010 | Martin et al. |
| 7,745,210 B2 | 6/2010 | Martin |
| 7,820,431 B2 | 10/2010 | Kenney et al. |
| 7,867,761 B2 | 1/2011 | Esser et al. |
| 7,897,379 B2 | 3/2011 | Kenney et al. |
| 7,964,392 B2 | 6/2011 | Hatano et al. |
| 8,039,252 B2 | 10/2011 | Berry |
| 8,114,646 B2 | 2/2012 | Martin et al. |
| 2001/0055803 A1 | 12/2001 | Wall et al. |
| 2003/0054544 A1 | 3/2003 | Gruenberg |
| 2003/0186428 A1 | 10/2003 | Guillot et al. |
| 2004/0029265 A1 | 2/2004 | Doi et al. |
| 2004/0043481 A1 | 3/2004 | Wilson |
| 2004/0132175 A1 | 7/2004 | Vetillard et al. |
| 2004/0152149 A1 | 8/2004 | Reid et al. |
| 2004/0203147 A1 | 10/2004 | Triffitt et al. |
| 2005/0101009 A1 | 5/2005 | Wilson et al. |
| 2005/0106717 A1 | 5/2005 | Wilson et al. |
| 2005/0239198 A1 | 10/2005 | Kunas et al. |
| 2005/0239199 A1 | 10/2005 | Kunas et al. |
| 2006/0205065 A1 | 9/2006 | Bossi et al. |
| 2007/0026516 A1 | 2/2007 | Martin et al. |
| 2007/0031963 A1 | 2/2007 | Chang et al. |
| 2007/0065933 A1 | 3/2007 | Esser et al. |
| 2007/0254356 A1 | 11/2007 | Wilson et al. |
| 2008/0003671 A1 | 1/2008 | Martin |
| 2008/0118974 A1 | 5/2008 | Martin et al. |
| 2008/0176318 A1 | 7/2008 | Wilson et al. |
| 2008/0227176 A1 | 9/2008 | Wilson |
| 2008/0299649 A1 | 12/2008 | Martin et al. |
| 2009/0191620 A1 | 7/2009 | Martin et al. |
| 2009/0298163 A1 | 12/2009 | Bennett et al. |
| 2009/0298164 A1 | 12/2009 | Cattadoris et al. |
| 2010/0129900 A1 | 5/2010 | Clark et al. |
| 2010/0233797 A1 | 9/2010 | Daly |
| 2010/0273251 A1 * | 10/2010 | Rhoads et al. ............ 435/290.1 |
| 2010/0304472 A1 | 12/2010 | Kim et al. |
| 2011/0258915 A1 | 10/2011 | Subhadra |
| 2011/0287541 A1 | 11/2011 | Cuello et al. |

FOREIGN PATENT DOCUMENTS

| | | |
|---|---|---|
| GB | 1 539 263 | 1/1979 |
| GB | 2 268 187 A | 1/1994 |
| WO | 93/10211 | 5/1993 |
| WO | 99/02646 | 1/1999 |
| WO | 2004/076609 A1 | 9/2004 |
| WO | 2005/035728 A2 | 4/2005 |
| WO | 2005/044972 A2 | 5/2005 |
| WO | 2005/047453 A1 | 5/2005 |
| WO | 2005/066328 A1 | 7/2005 |
| WO | 2006/099127 A1 | 9/2006 |
| WO | 2007/015770 A1 | 2/2007 |
| WO | 2008/069902 A2 | 6/2008 |
| WO | 2008073313 A2 | 6/2008 |
| WO | 2008073314 A2 | 6/2008 |
| WO | 2008106012 A1 | 9/2008 |
| WO | 2008153783 A1 | 12/2008 |
| WO | 2009094125 A2 | 7/2009 |
| WO | 2009136907 A1 | 11/2009 |
| WO | 2009148512 A2 | 12/2009 |
| WO | 2010/008566 A2 | 1/2010 |
| WO | 2010006055 A2 | 1/2010 |
| WO | 2010099264 A2 | 9/2010 |

* cited by examiner

MULTILAYER TISSUE CULTURE VESSEL

FIELD OF THE INVENTION

The present invention relates to laboratory vessels. More particularly, the present invention relates to multilayer tissue culture vessels.

BACKGROUND OF THE INVENTION

Cells, such as eukaryotic cells, are cultured for a variety of purposes, including basic research and high-throughput screening. However, culturing cells under sterile conditions is both laborious and expensive. Thus, there is a need for more efficient and cost-effective laboratory vessels for culturing cells.

SUMMARY OF THE INVENTION

The present invention discloses a vessel for culturing cells which includes: a bottom including a base with an upwardly extending wall at least partially bounding the base of the bottom; a top including a base with a downwardly extending wall at least partially bounding the base of the top; a tubular neck with an opening defined therein; and, one or more shelves, wherein, each shelf includes a base with an upwardly extending wall at least partially bounding the base of the shelf. The upwardly extending wall of a first shelf adjoins the downwardly extending wall of the top with the first shelf being located intermediate the bottom and the top. The base of each of the shelves having at least one aperture formed therein. The bottom, the top and the one or more shelves collectively define an enclosed volume for culturing cells. The tubular neck extends from the vessel with the enclosed volume being accessible by the opening in the tubular neck. Advantageously, this vessel provides high volume cell culture in a manner that increases efficiency and reduces the cost of culturing cells.

The vessels of the present invention increase the total culture area per surface area of the footprint of a culture vessel. The vessels also increase the percent recovery of cells per surface area of the footprint of a culture vessel. Thus, the vessels provide means for efficient high volume cell culture. Such vessels may be used in a manual and/or automated fashion. Exemplary embodiments include, but are not limited to, vessels which maintain the general footprint of a standard BD Falcon T-175 flask, and are thus compatible with automated cell culture systems, such as The Automation Partnership's SelecT™ and CompacT™ automated cell culture systems. The vessels, however, may be expanded or reduced in comparison to the height of a standard flask, such as a BD Falcon T-175 flask. In particular, the stacking arrangement of shelves within the vessel permits the height to be varied such that the surface area for culturing cells can be expanded.

In addition, the vessel's design minimizes the number of manipulations required to fill and remove media thereby increasing the efficiency of culturing cells and decreasing the chance for contamination of the vessel with each movement. Preferably, the vessels include an opening sufficiently large for a pipette to access the back wall of the vessel thereby promoting good laboratory practices for good cell culture technique. Exemplary embodiments may include, but are not limited to, vessels wherein the opening is sufficiently large for a 10 mL pipette or even for a 50 mL pipette to access the back wall.

The vessels' design also decreases the amount of media as well as cells "hung up" along the walls and corners of the vessel's interior and allows for efficient removal of media and cells. The vessels' design also distributes liquid (e.g., media, phosphate buffered saline (PBS), trypsin) efficiently to the different layers of cells thereby decreasing the amount of liquid required, promoting more even distribution of liquid and promoting more even cell distribution during seeding. This provides more consistent distribution of nutrients, nutrient consumption rate, cell growth rate and dissociation rate at the time of cell harvest thereby fostering more uniform cell growth and/or differentiation as well as a healthier population of cells overall. Such vessels also provide a great cost savings with respect to the amount of media and dissociation agent (e.g., trypsin) required for cell growth and dissociation of cells, respectively. In short, the vessels of the present invention decrease the amount of labor and expense associated with culturing cells.

These and other features of the invention will be better understood through a study of the following detailed description and accompanying drawings.

DETAILED DESCRIPTION OF THE INVENTION

With reference to the Figures, a vessel 10 for cell culturing is depicted. The vessel 10 may be utilized with various cell cultures, as will be appreciated by those skilled in the art. The vessel 10 generally includes a bottom 12, a top 14, a tubular neck 16, having an opening 18 defined therein, and one or more shelves 20 located intermediate the bottom 12 and the top 14. The bottom 12, the top 14 and the shelves 20 collectively define an enclosed volume 22 for culturing cells. The tubular neck 16 extends from the vessel 10, with the enclosed volume 22 being accessible by the opening 18 in the tubular neck 16.

The bottom 12 is generally tray-shaped with a base 24 from which upwardly extends a wall 26 which at least partially bounds the base 24. Preferably, the wall 26 fully bounds the base 24 perimetrically.

Depending on the overall desired size of the vessel 10, one or more of the shelves 20 may be utilized. The greater the quantity of the shelves 20, the greater the cell culturing capacity of the vessel 10. Due to limits in gas flow and distribution, excessive size may not be desired. Embodiments utilizing two or four of the shelves 20 are envisioned. However, other quantities may be utilized. Each of the shelves 20 is generally tray-shaped having a base 28 with a wall 30 extending upwardly therefrom to at least partially bound the base 28. Preferably, the wall 30 fully perimetrically bounds the base 28 for each of the shelves 20. In addition, at least one aperture 32 is formed through the base 28 of each of the shelves 20. Preferably, each of the shelves 20 includes at least two apertures 32, a gas-transmission aperture 32a and a flow aperture 32b. As discussed further below, the gas-flow apertures 32a permit gas transmission through the shelves 20 so as to permit gas flow throughout the vessel 10. The flow apertures 32b may be provided for equilibrating cell media disposed into the vessel 10 so as to distribute the cell media between the various support layers of the vessel 10 as defined by the bottom 12 and the shelves 20. Although it is preferred to utilize a two-aperture arrangement for each of the shelves 20, a single aperture 32 may be provided for each of the shelves 20 which may perform both functions of gas transmission and equilibration. Further, more than two apertures 32 may be utilized for one or both of the functions of gas transmission and equilibration. It is preferred that the gas-transmission aperture 32a and the flow aperture 32b of a respective shelf 20 be spaced apart.

The top 14 has a generally inverted tray-shape with a base 34 and a wall 36 which extends downwardly therefrom to at least partially bound the base 34. Preferably, the tubular neck 16 is formed integrally with the top 14 so as to extend therefrom. Alternatively, an opening may be formed in the top 14, with the tubular neck 16 being formed as a separate component which is secured to the top 14 using any known technique, such as fusion or adhesive. It is further possible to form an opening which extends from the top 14 and into one or more of the shelves 20 to which the tubular neck 16 is attached. The opening 18 in the tubular neck 16 may be elliptical (including being circular) or semi-circular and may be formed with a constant or variable profile along the length of the tubular neck 16 (e.g., a portion of the opening 18 may be elliptical and a portion may be semi-circular along the length of the tubular neck 16).

The bottom 12, the top 14 and one or more of the shelves 20 are arranged in a stacked fashion so as to collectively form the vessel 10. Preferably, the components are formed of a thermoplastic material which is compatible with the cells of interest. Polystyrene may be utilized. As will be appreciated by those skilled in the art, other materials may be utilized. The components may be formed clear, tinted (e.g., blue tint) or colored (e.g., amber). In addition, various portions of the bottom 12, the top 14, and the shelves 20 may be modified or treated so as to enhance certain conditions. For example, one or more biological agents may be applied to one or more portions of the bottom 12, the top 14 and/or the shelves 20, including, but not limited to, an extracellular matrix, or components thereof, such as laminin, fibronectin, and collagen, in any combination. In addition, or alternatively, synthetic agents may be applied. The surfaces may also be pre-treated, such as with tissue-culture treatment or plasma polymerization. As will be appreciated by those skilled in the art, these various treatments or modifications may be used in various combinations and utilized depending on intended objectives.

The bottom 12, the top 14 and the shelves 20 are adjoined to form the vessel 10. In particular, the wall 36 of the top 14 is adjoined to the wall 30 of the shelf 20 located adjacent to the top 14. All of the shelves 20 are located intermediate the bottom 12 and the top 14. Adjacent shelves 20 are arranged in stacked fashion and adjoined with the wall 30 of the lower stacked shelf 20 being adjoined to the higher stacked adjacent shelf 20. The bottom 12 is adjoined to the shelf 20 adjacent to the bottom 12, which shall be the lowest stacked shelf 20 if a plurality of the shelves 20 is utilized, with the wall 26 of the bottom 12 being adjoined to the adjacent shelf 20. Any known technique, such as fusion (e.g., by ultrasonic welding), adhesion, and/or mechanical interconnections (e.g., interlocking tongue and groove) may be utilized in any combination, so as to provide liquid-tight seals at the interfaces thereof. Sealing members, such as gaskets, may be interposed between adjacent components, such as between the top 14 and the adjacent shelf 20. The gasket material may be chosen so as to be gas permeable, but liquid impermeable. In addition, one or more vented openings 37 may be formed in the bottom 12, the top 14 and/or one or more of the shelves 20. A gas permeable/liquid impermeable membrane 39 may be provided to extend across one or more of the vented openings 37.

The bottom 12, the top 14 and the shelves 20 may be sized with various shapes to provide different surface areas for cell culturing. Accordingly, the vessel 10 may be formed with different dimensions and different shapes, such as a flask shape, as shown in the figures. Alternatively, the vessel 10 may have a rectangular shape, or be formed of other polygonal or other shapes. Preferably, the vessel 10 includes a first end 38 formed to support the vessel 10 in an upright position where the shelves 20 are aligned upwardly. This is a preferred state for loading cell media to achieve equilibration. More preferably, the first end 38 is located at an opposite location on the vessel 10 from the opening 18 of the tubular neck 16. The first end 38 may be a flat surface or a locus of points which collectively define a resting surface.

The bottom 12, the top 14 and the shelves 20 form the vessel 10. The walls 26, 30, 36 of the bottom 12, the top 14 and the shelves 20, respectively, and the bases 24, 28 of the bottom 12 and the top 14, respectively, define portions of the exterior surface of the vessel 10.

Figure 16:
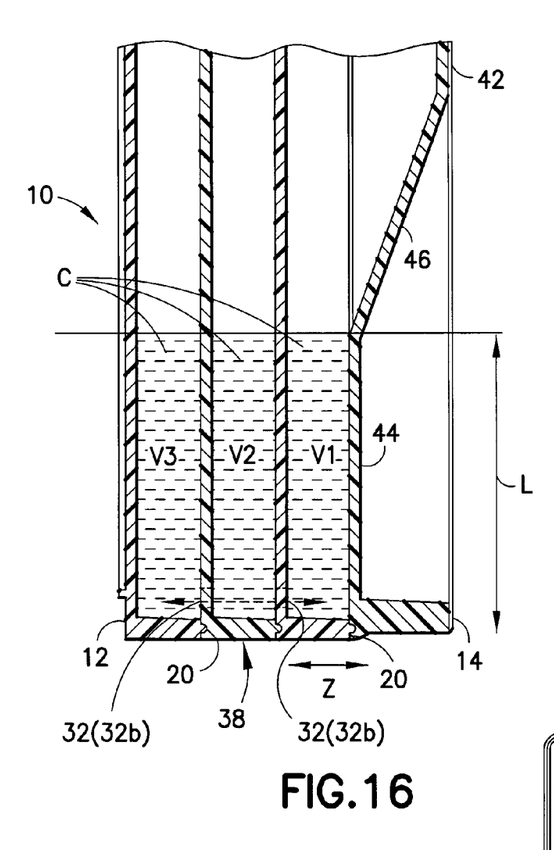
FIG. 16 is a schematic demonstrating equilibration of cell media in a vessel formed in accordance with the subject invention.
Figure 18:
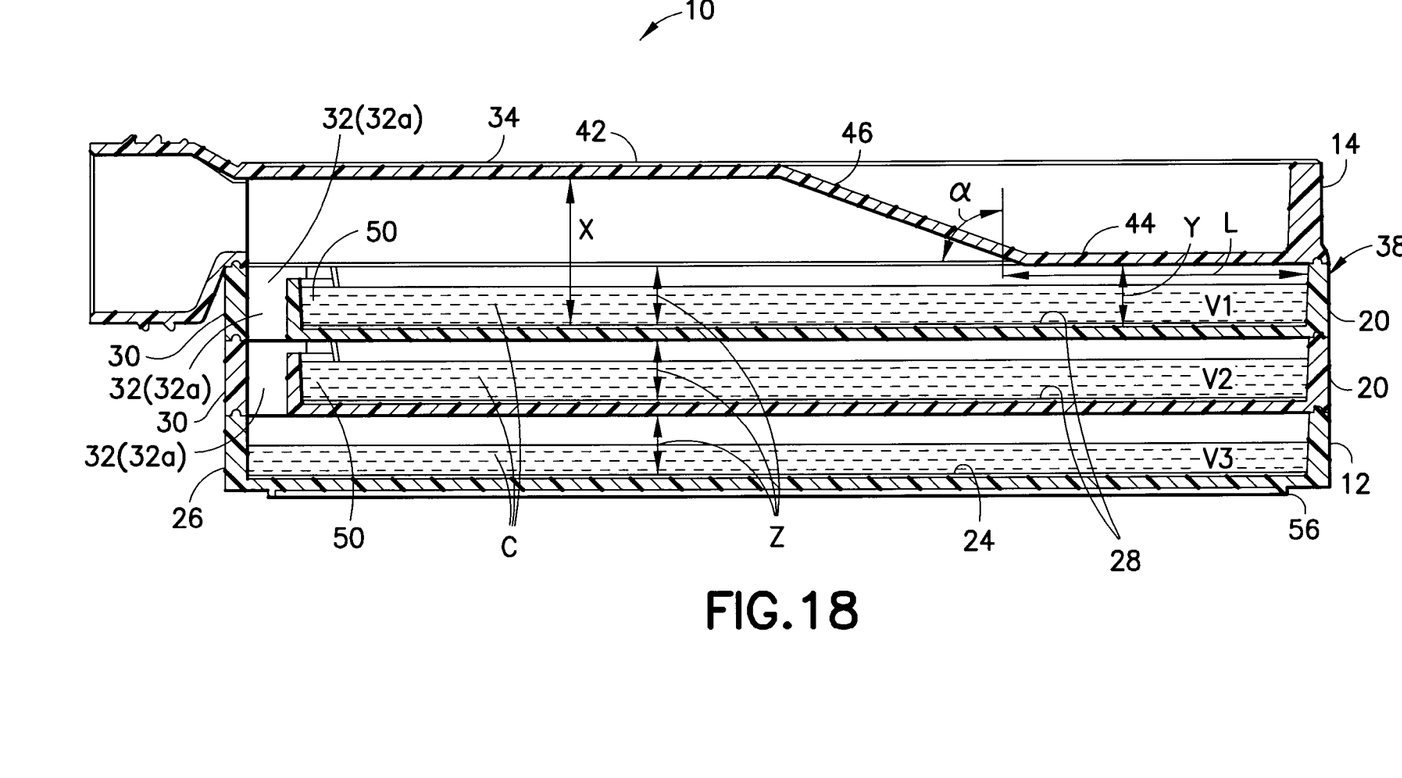
FIG. 18 is a schematic demonstrating layered arrangement of cell media in a vessel formed in accordance with the subject invention.

To achieve equilibration, it is preferred that the flow apertures 32b be located in proximity to the first end 38. In this manner, as shown in FIG. 16, with cell media C being disposed in the vessel 10, and with the vessel 10 resting on the first end 38, the cell media C may pass through the flow apertures 32b and achieve divided volumes ($V_1, V_2, V_3\ldots$) in an equilibrated state between the bottom 12, the shelves 20 and the top 14. From the equilibrated state, the vessel 10 is caused to be placed horizontally resting on the bottom 12, as shown in FIG. 18. The divided amounts of the cell media C are thus caused to spread across the supporting underlayer, which may be defined by the bottom 12 or the shelves 20.

Preferably, the cell media C is caused to equilibrate into equal volumes between the bottom 12, the shelves 20 and the top 14. Equal spacing, such as spacing z, between the bases 24, 28 and 34 of the bottom 12, the top 14 and the shelves 20, respectively, can cause equal volumes to be entrapped between the layers, particularly adjacent to the first end 38 of the vessel 10.

Figure 13:
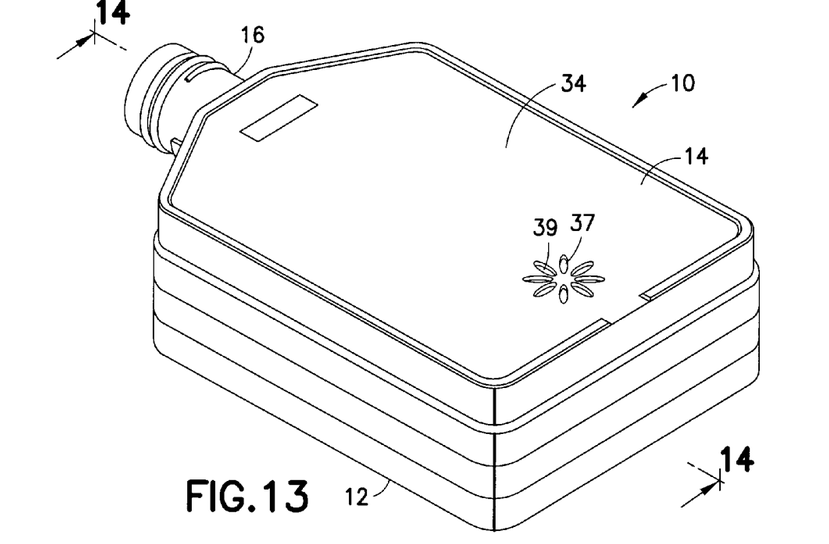
FIG. 13 is a perspective view of a vessel formed in accordance with the subject invention.
Figure 14:
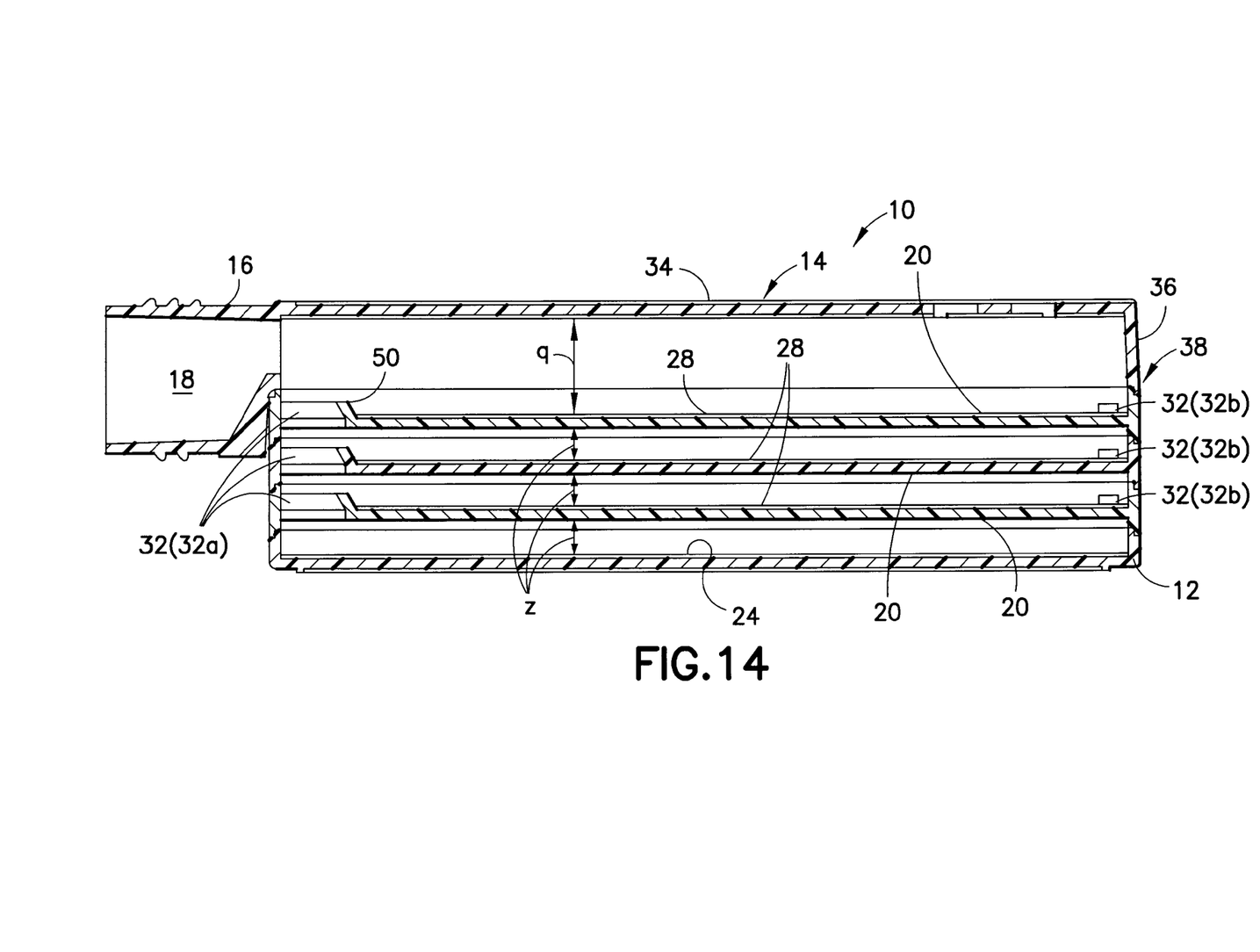
FIG. 14 is a cross-sectional view taken along line 14-14 of FIG. 13.
Figure 17:
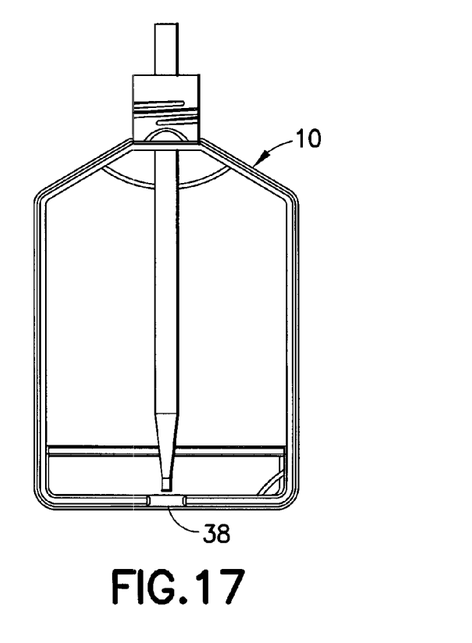
FIG. 17 is a schematic demonstrating pipette access in a vessel formed in accordance with the subject invention.

As shown in FIGS. 13-14, the base 34 of the top 14 may be formed generally planar throughout. To permit good pipette access, the base 34 of the top 14 may have portions thereof spaced from the base 28 of the adjacent shelf 20 greater than the spacing z found between the bases 28 of the shelves 20 or between the base 24 of the bottom 12 and the base 28 of the adjacent shelf 20, as shown in FIG. 14. This increased spacing (spacing q) enhances pipette access through the entire length of the vessel 10 into contact with the first end 38, as shown in FIG. 17. Thus, post cell culturing, and with the vessel 10 resting on the first end 38, efficient recovery of cell media and cells may be conducted utilizing the pipette access. Increased spacing, however, between the base 34 of the top 14 and the base 28 of the adjacent shelf 20 may result in an enlarged volume being entrapped between the top 14 and the adjacent shelf 20 as compared to the volumes entrapped between the shelves 20 and the volume entrapped between the bottom 12 and the adjacent shelf 20.

Preferably, the base 34 of the top 14 is formed with first, second and third portions, 42, 44, 46, respectively, which reduce the volume entrapped between the base 34 of the top 14 and the base 28 of the adjacent shelf 20 in proximity to the first end 38. In particular, with reference to FIG. 18, the first portion 42 is located a distance x from the base 28 of the adjacent shelf 20, the second portion 44 is located a distance y from the base 28 of the adjacent shelf 20, with the distance x being greater than the distance y. The second portion 44 extends from the first end 38 so as to partially enclose the volume adjacent to the first end 38. Preferably, the distance y is equal to the spacing z set between each adjacent pairs of the shelves 20 and between the bottom 12 and the adjacent shelf 20. It is further preferred that the second portion 44 have a predetermined length L extending from the first end 38 which is equal to or greater than the length necessary to accommodate the target equilibrated volume. In this manner, as shown in FIG. 16, with the cell media C being equilibrated, the second portion 44 extends coextensively with or beyond the height of the cell media C (as equilibrated as volumes $V_1, V_2, V_3...$). It is preferred to have the height of the cell media C be below the third portion 46 in the equilibrated state. Height of the cell media C above the second portion 44 and into contact with the third portion 46 may result in uneven volumes resulting from equilibration. With the arrangement of the first, second and third portions 42, 44, 46, good pipette access may be provided to the first end 38, which includes access to the volume adjacent to the second portion 44 in proximity to the first end 38, with the pipette passing through the greater height area adjacent to the first portion 42. This arrangement also permits for equal volumes to be equilibrated between the various layers. The first and second portions 42, 44 may be each formed flat and may be arranged in parallel although other configurations (e.g., arcuate) are useable.

The third portion 46 of the base 34 extends between and joins the first and second portions 42, 44. Preferably, the third portion 46 is formed flat, but may be formed with other shapes, such as with an arcuate profile. Advantageously, the third portion 46 may define a suitable surface for printing or for bearing other indicia, such as bar coding. With respect to a plane defined by the second portion 44, the third portion 46 is disposed at an angle $\alpha$ in the range of about 10-90 degrees, more preferably in the range of about 10-30 degrees, and more preferably at the angle $\alpha$ of about 20 degrees. The third portion 46, as being disposed angularly relative to the second portion 44, provides a tapered surface which directs the cell media C towards the first end 38 with the vessel 10 resting on the first end 38. Although an angle $\alpha$ of 90 degrees is possible, it is preferred that the angle $\alpha$ be less than 90 degrees so as to prevent any cell media or cells being trapped at the intersection of the first and third portions 42, 46.

Figure 1:
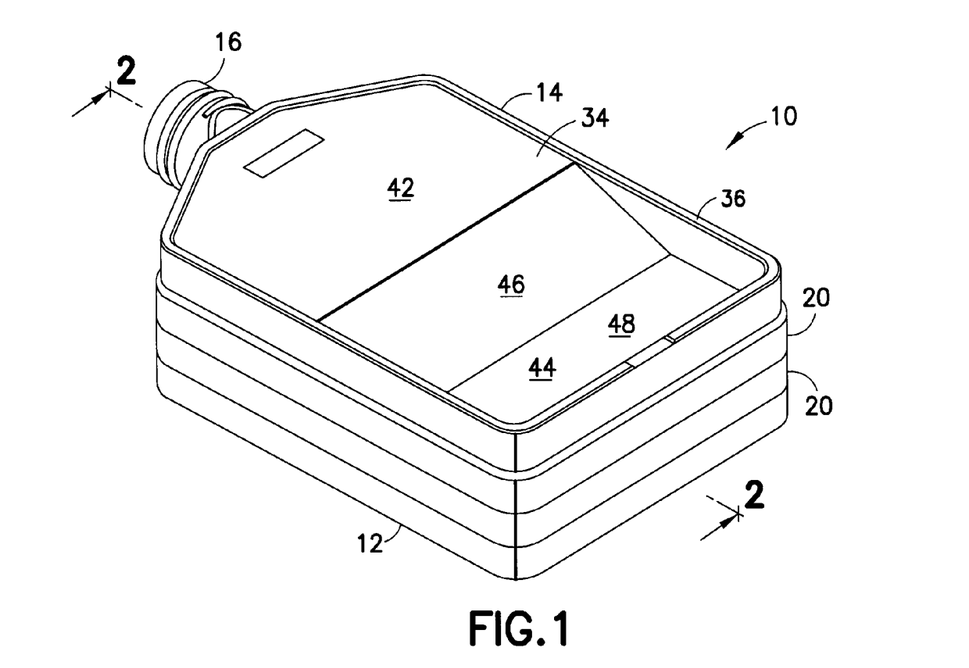
FIG. 1 is a perspective view of a vessel formed in accordance with the subject invention.

With the use of the second portion 44, as shown in FIG. 1, a recess 48 may be defined in the vessel 10. The wall 36 of the top 14 may partially bound the recess 48. The recess 48 provides a handle function in exposing portions of the wall 36 in permitting gripping access thereto for a user.

Figure 2:
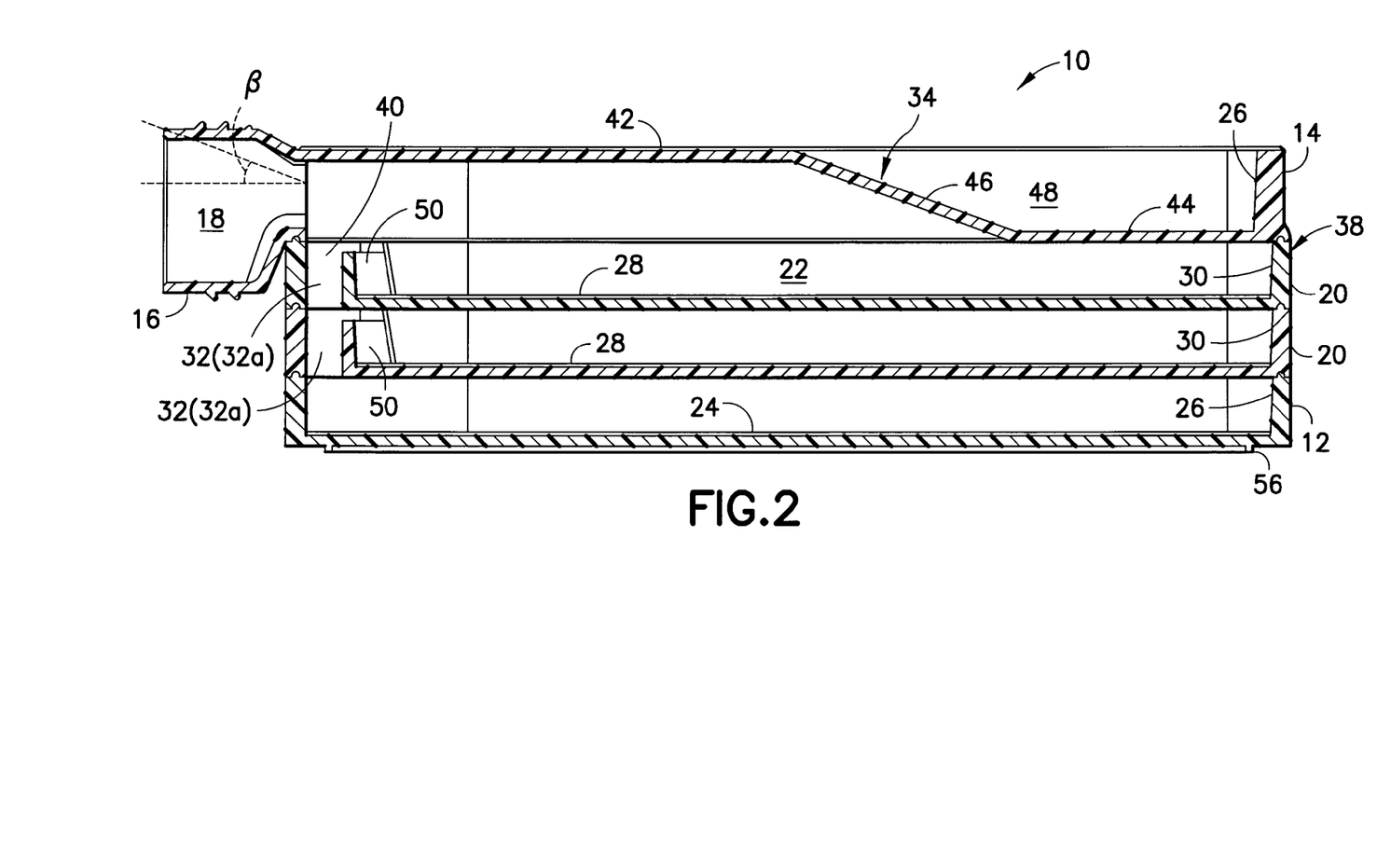
FIG. 2 is a cross-sectional view taken along line 2-2 of FIG. 1.
Figure 3:
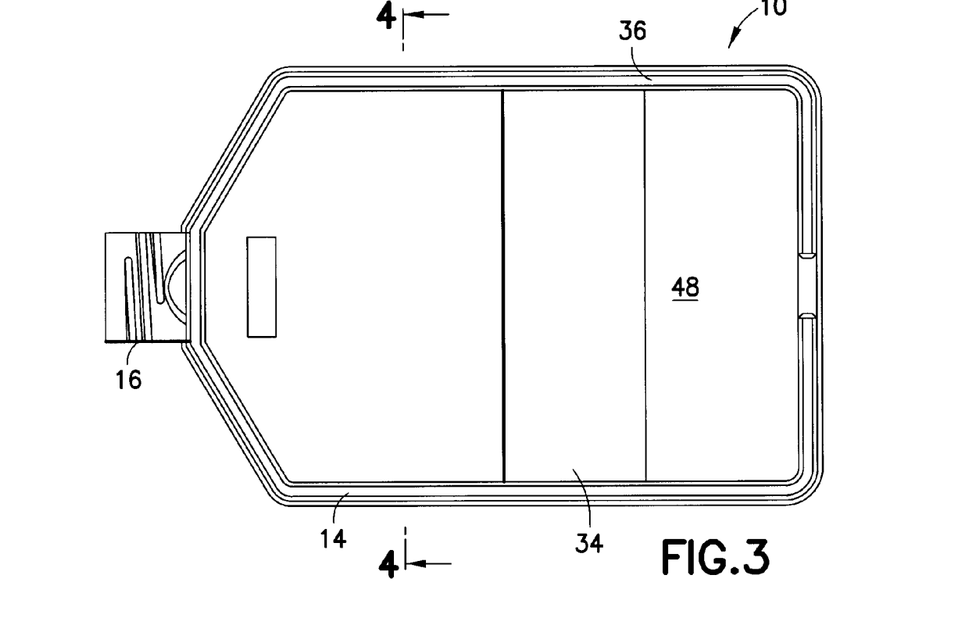
FIG. 3 is a top plan view of the vessel.
Figure 4:
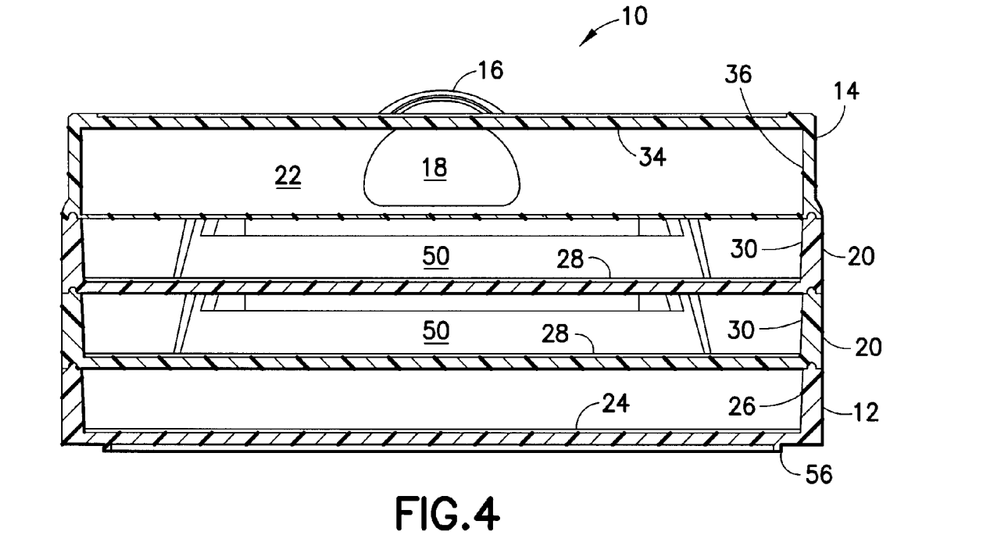
FIG. 4 is a cross-sectional view taken along line 4-4 of FIG. 3.
Figure 5:
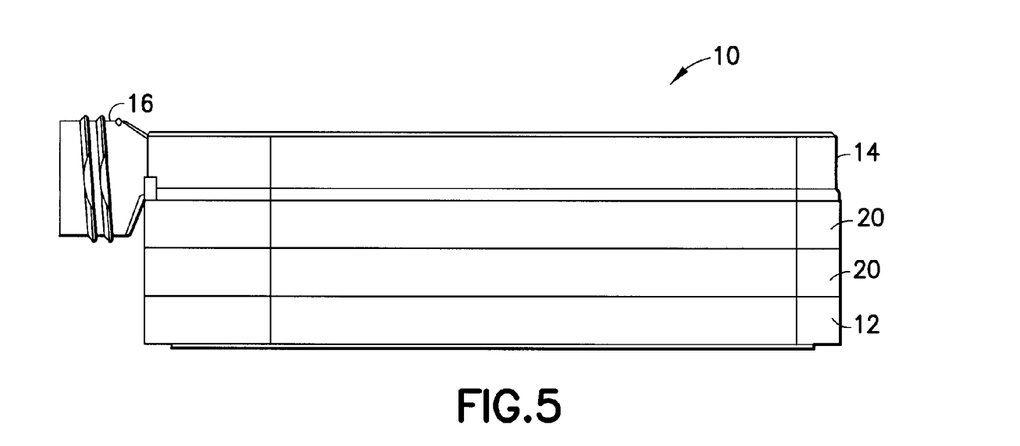
FIG. 5 is a side view of the vessel.
Figure 6:
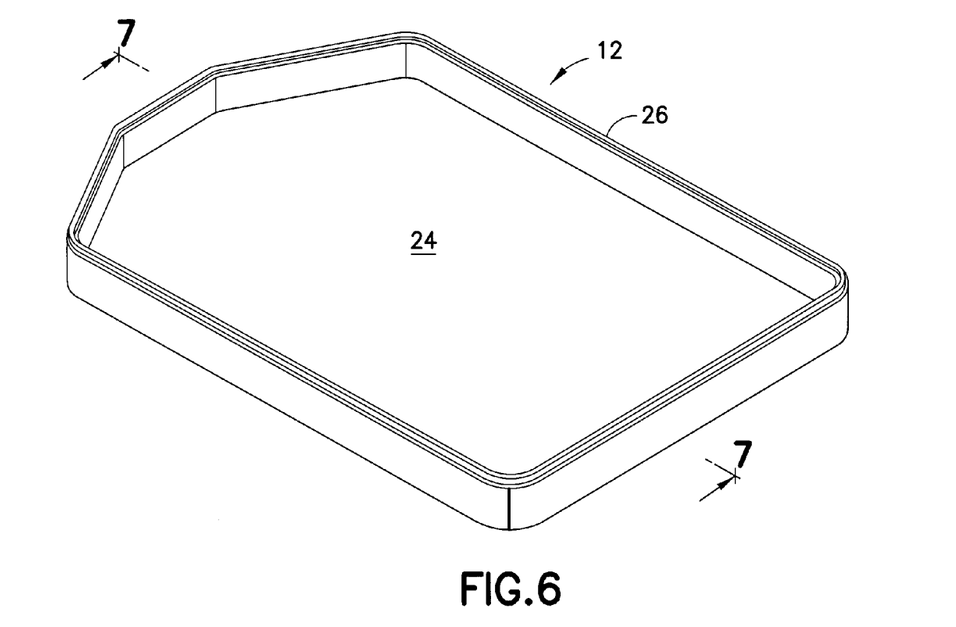
FIG. 6 is a perspective view of a bottom useable with the subject invention.
Figure 7:
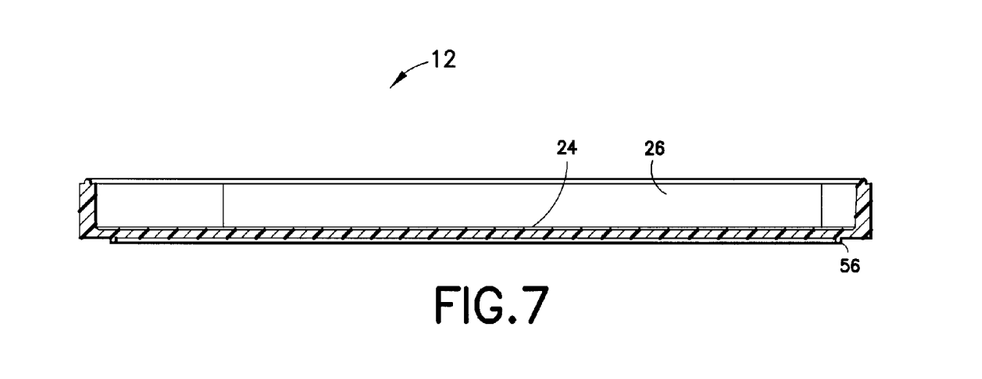
FIG. 7 is a cross-sectional view taken along line 7-7 of FIG. 6.
Figure 8:
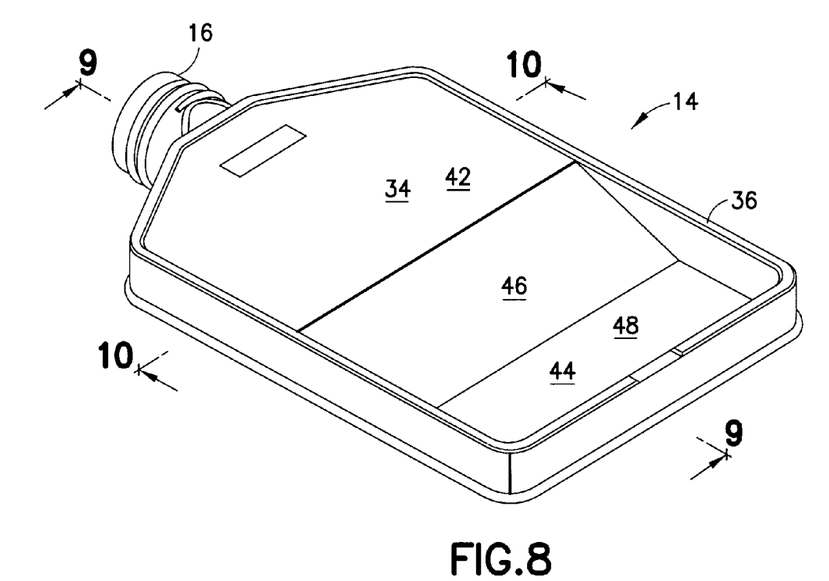
FIG. 8 is a perspective view of a top useable with the subject invention.
Figure 9:
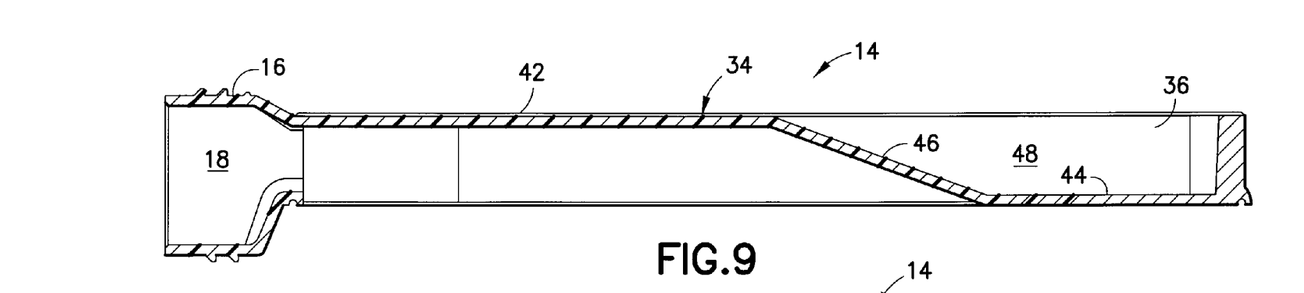
FIG. 9 is a cross-sectional view taken along line 9-9 of FIG. 8.
Figure 10:
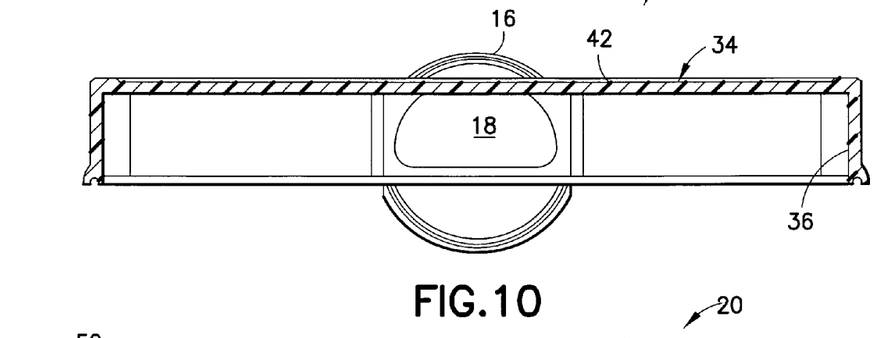
FIG. 10 is a cross-sectional view taken along line 10-10 of FIG. 8.

As shown in FIG. 2, it is preferred that the gas-transmission apertures 32a be in linear registration so as to define a gas flow channel 40 inside the enclosed volume 22. Preferably, the gas flow channel 40 extends into proximity to the opening 18 defined in the tubular neck 16. The gas flow channel 40, by extending through the shelves 20, permits gas flow to reach various portions of the enclosed volume 22.

As discussed above, and shown in FIG. 18, in a cell culturing use state, the vessel 10 is disposed to rest on the bottom 12. In this position, the cell media C, due to its liquid nature, is disposed across the face of the base 24, 28 of the corresponding bottom 12 or shelf 20. With respect to the bottom 12, the wall 26 provides fluid containment in maintaining the cell media C atop the base 24. With respect to the shelves 20, to provide containment in preventing the cell media C from passing through any of the apertures 32 (32a, 32b), a containment wall 50 may be disposed along the edge of each of the apertures 32 to act as a levee. Preferably, the height of the walls 30 of the shelves 20 is greater than the height of the containment walls 50. In this manner, an open space can be maintained above each layer of the cell media C between the shelves 20.

The bottom 12 and the shelves 20 may be configured to handle different volumes of the cell media C, although it is preferred that within the same vessel 10, the same volume is accommodated for each layer. The base 24 and the wall 26 of the bottom 12 define the volume for receiving the cell media C on the bottom 12. The base 28, the wall 30, and the containment wall(s) 50 of each of the shelves 20 define the volume for receiving the cell media C thereupon. The bottom 12 and the shelves 20 may be configured to each accommodate a volume of the cell media C in the range of 4-50 mL. The surface area of the bottom 12 may be greater than the surface area of each of the shelves 20, as the bottom 12 has none of the apertures 32 formed therein; as such, the height of the cell media C layer on the bottom 12 may have a slightly lower height than the height of the cell media C layers on the shelves 20. The spacing z is set to take into consideration the amount of volume of the cell media C for each layer to ensure sufficient head-space above the layer of the cell media C for proper gas distribution.

Figure 11:
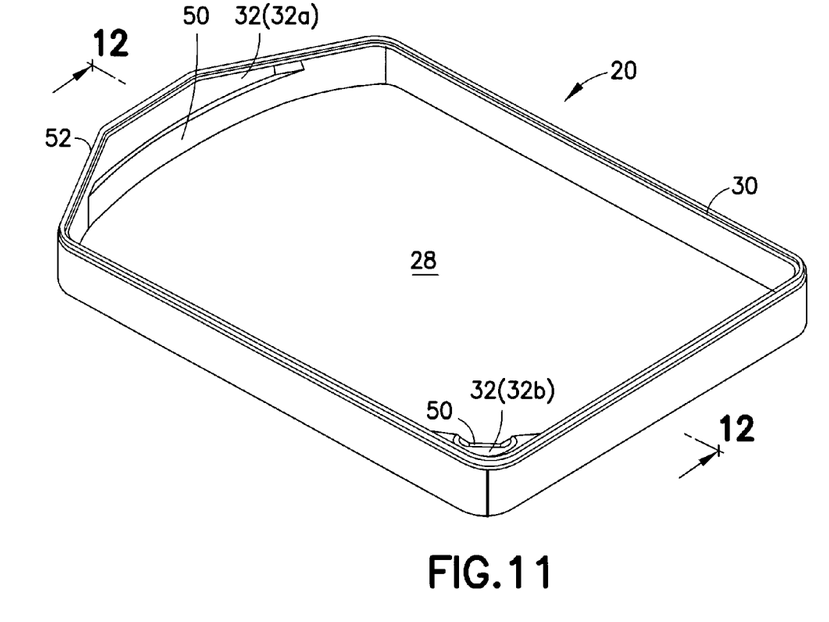
FIG. 11 is a perspective view of a shelf useable with the subject invention.
Figure 12:
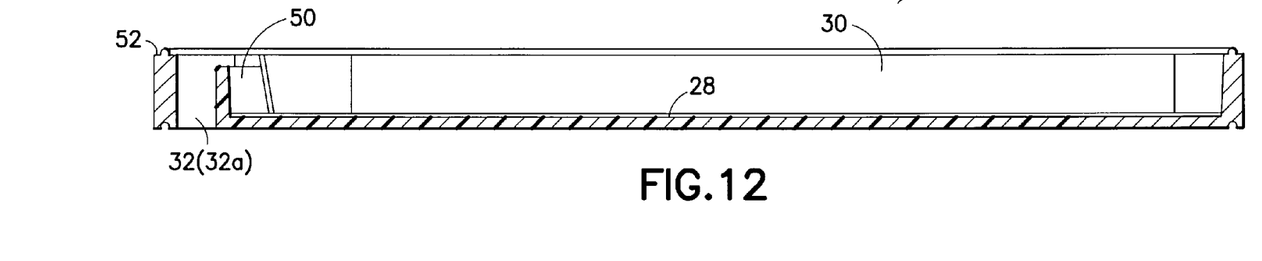
FIG. 12 is a cross-sectional view taken along line 12-12 of FIG. 11.
Figure 15:
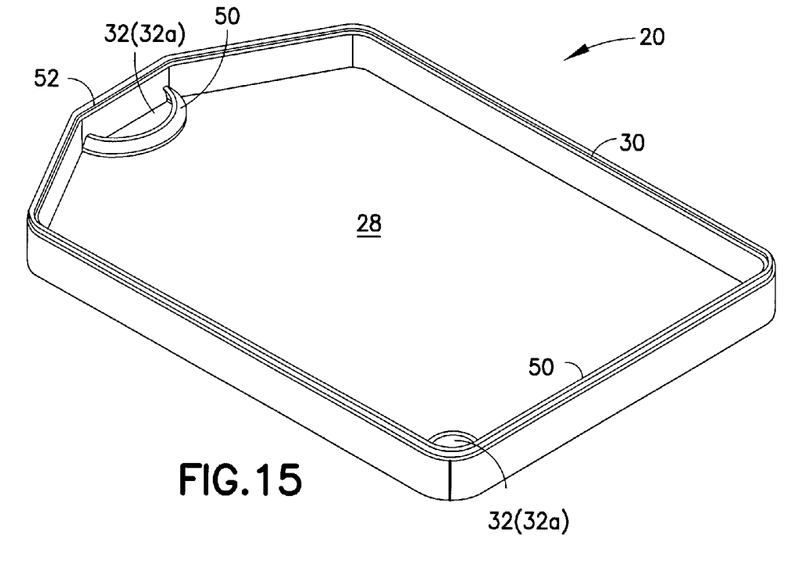
FIG. 15 is a perspective view of a shelf useable with the subject invention.
Figure 19:
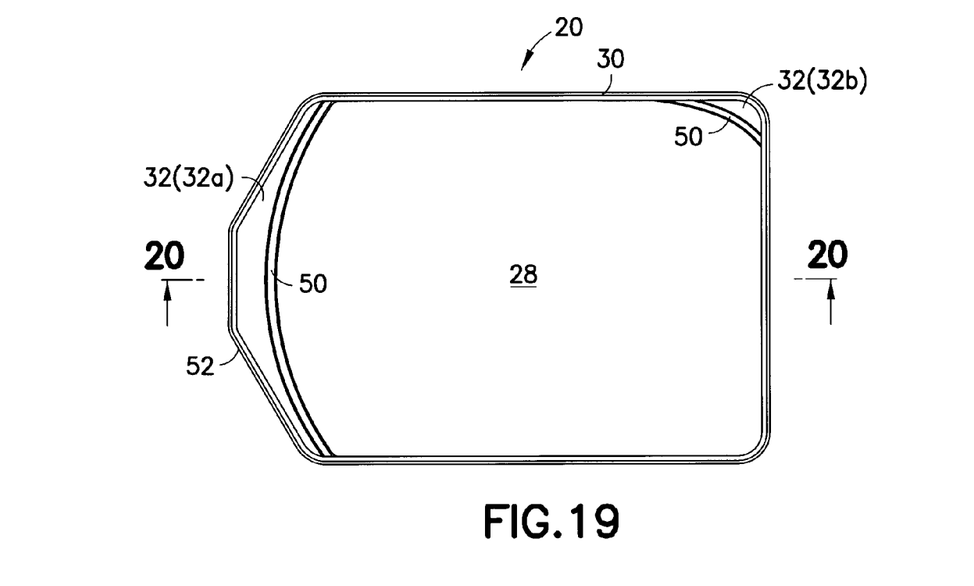
FIG. 19 is a top plan view of a shelf useable with the subject invention.
Figure 20:
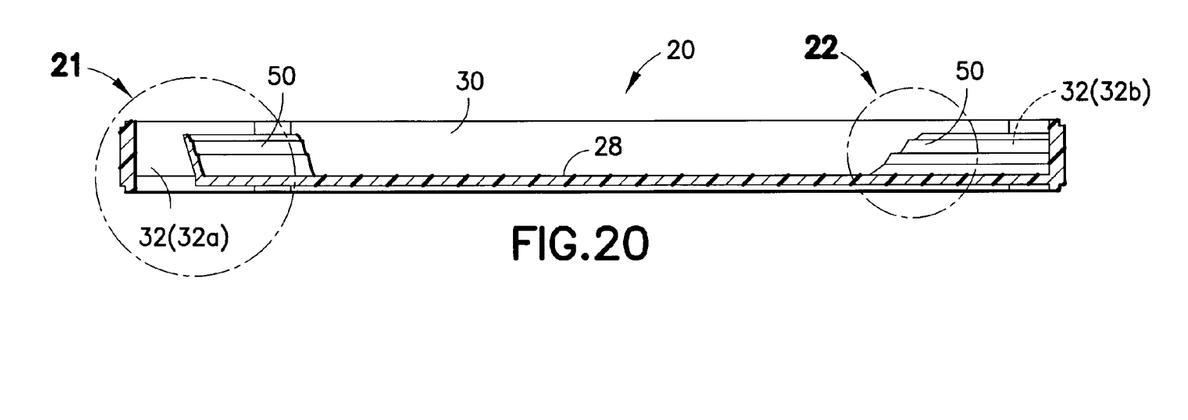
FIG. 20 is a cross-sectional view taken along line 20-20 of FIG. 19.
Figure 21:
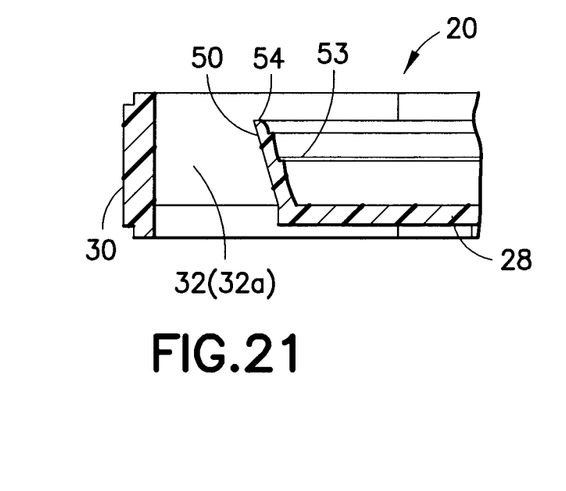
FIGS. 21 and 22 are enlarged views of Sections 21 and 22, respectively, of FIG. 20.
Figure 22:
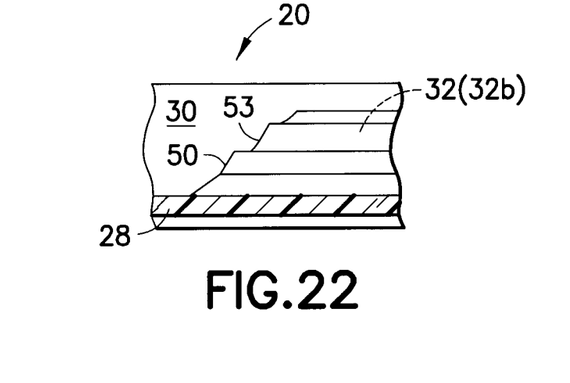
Figure 23:
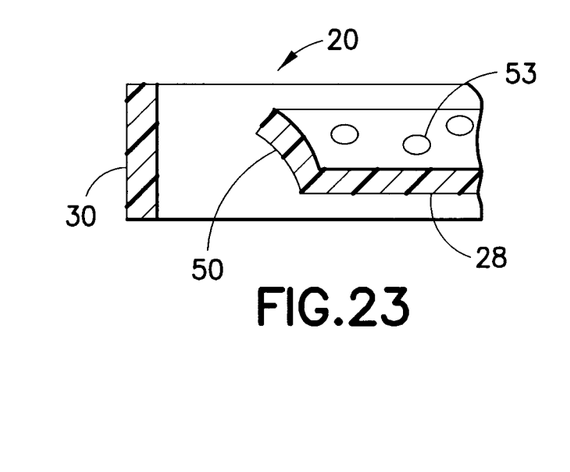
FIGS. 23 and 24 depict different containment wall configurations.
Figure 24:
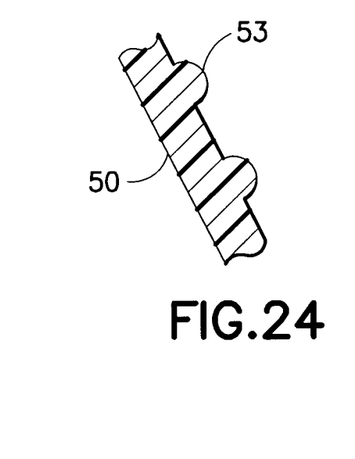

Concerns exist over the cell media C being wicked by the containment walls 50 into the corresponding apertures 32. It is preferred that the containment walls 50 be bowed along an arcuate longitudinal axis, as shown in FIGS. 11, 15 and 19. The bowed shape acts against capillary attraction and provides an anti-wicking effect to the containment walls 50. The apertures 32 (32a, 32b) may be formed with arcuate shapes with the containment walls 50 being disposed along edges thereof. In addition, as shown in FIGS. 11, 15 and 19, the apertures 32 may have various configurations. In particular, the gas-transmission apertures of 32a may be formed to extend across a portion of a side edge 52 of the shelves 20 (FIGS. 11 and 15) or be formed to extend along the full length of the side edge 52 of the shelves 20 (FIG. 19).

The containment walls 50 may be provided with other anti-wicking features such as being angularly disposed relative to the base 28 of the respective shelf 20 (FIG. 21); being provided with arcuate cross-sections (FIG. 23); and/or, include non-smooth surfaces 53 facing away from the corresponding aperture 32. The non-smooth surface 53, as shown in FIGS. 20-24, may include various surface interruptions or protrusions, such as bumps, dimples, roughened areas, striations, and the like. The anti-wicking features are intended to disrupt capillary attraction. In addition, or alternatively, the containment walls 50 may be made or prepared to have hydrophobic portions to repel the cell media C. For example, free edges 54, at which the containment walls 50 terminate, may be prepared to be hydrophobic. Other portions of the containment walls 50 may be likewise treated. To further enhance this effect, portions of the bases 28 of the shelves 20 may be formed hydrophilic so as to enhance the retentiveness of the cell media C on the bases 28 of the shelves 20. These various anti-wicking features may be used in various combinations.

Figure 25:
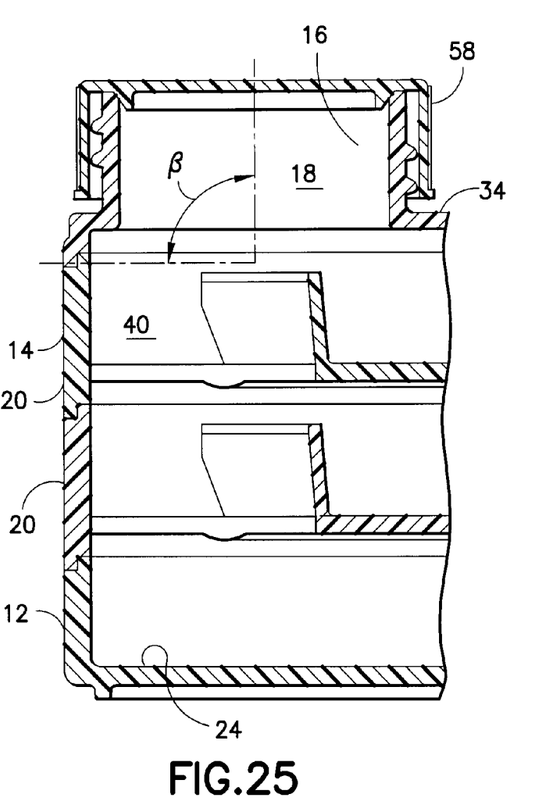
FIGS. 25-27 depict caps useable with the subject invention.
Figure 26:
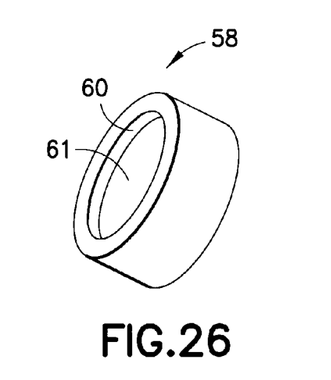
Figure 27:
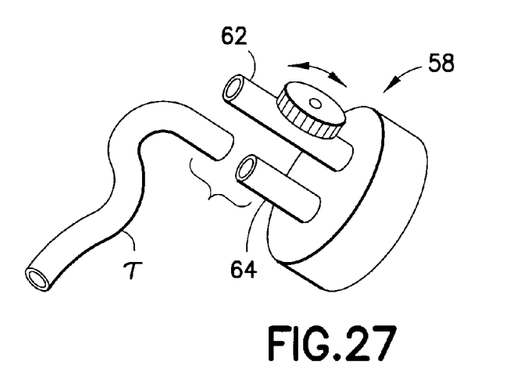

The vessel 10 may be provided with additional features or variations. For example, with reference to FIGS. 2 and 25, the tubular neck 16 may be provided at different angular orientations relative to the vessel 10. As shown in FIG. 2, the tubular neck 16 extends along a longitudinal axis which is disposed at an angle β relative to a plane defined by the base 28 of the uppermost shelf 20. The angle β may be in the range of about 0 degrees-90 degrees. At 0 degrees, the tubular neck 16 protrudes from a side of the top 14, as shown in FIG. 2. At 90 degrees, the tubular neck 16 has a vertical orientation and protrudes from the base 34 of the top 14, as shown in FIG. 25. With this arrangement, pipette access may be provided through the gas flow channel 40 to the volume located adjacent to the base 24 of the bottom 12 for cell media or cell removal. The angle β may be alternatively an acute angle.

It is preferred that the vessel 10 be formed to be stackable with other vessels. To achieve such stacking, it is preferred that the top 14 define an upper resting surface which is parallel to a resting surface defined by the bottom 12. In this manner, two or more of the vessels 10 may be stacked with the bottom 12 of the upper-stacked vessel being supported by the top 14 of the lower-stacked vessel 10. To enhance stability, a bead 56 may be defined on the exterior surface of the bottom 12. Correspondingly, the wall 36 of the top 14 may be formed to slightly protrude from the base 34. The wall 36 may be formed to nestingly receive the bead 56 to provide lateral stability in a stacked configuration. It is noted that the wall 36 of the top 14, particularly by protruding from the base 34, may be configured to primarily bear the weight of the upper-stacked vessel 10. Instability issues due to the existence of the recess 48 may thus be avoided.

The bases 28 of the shelves 20 are preferably formed to be flat. Alternatively, the bases 28 may be formed with a rippled, wavy, or other configuration to increase surface area. With any configuration, it is preferred that the layers of the cell media C supported by the shelves 20 be disposed to be parallel with the vessel 10 resting on the bottom 12. The base 24 of the bottom 12 may be likewise configured to be rippled, wavy or otherwise formed to have increased surface area. With any configuration, it is preferred that the layer of the cell media C supported by the bottom 12 be parallel to the other layers of the cell media C.

The vessel 10 may be provided as an assembly with a corresponding cap 58 formed to mount onto the tubular neck 16 so as to seal the opening 18. Any known arrangement for permitting mounting, such as a friction-fit, interference-fit, threaded or bayonet mounting, may be utilized. The cap 58 may be formed solid so as to be non-vented. Alternatively, the cap 58 may be provided with one or more vents 60 which may include gas permeable/liquid impermeable membrane 61. Further, the cap 58 may include one or more adjustable valves 62 which permit selective aseptic connection between the enclosed volume 22 and an external fixture. Further, the cap 58 may include one or more tube connections 64 to permit direct and continuous communication with one or more supply tubes T (e.g., gas supply tubes).

In use, the vessel 10 is set upon the first end 38 and a sufficient amount of the cell media C is introduced into the enclosed volume 22 via the opening 18 to provide target volume amounts for the bottom 12 and each of the shelves 20. A pipette may be used to introduce the cell media C with the pipette being inserted through the opening 18 and into the enclosed volume 22 in between the top 14 and the adjacent shelf 20. The introduced cell media C collects in the volume adjacent to the first end 38 and equilibrates between the flow apertures 32b to provide divided volumes of the cell media C corresponding to the bottom 12 and each of the shelves 20. Once equilibrated, the vessel 10 is adjusted to rest on the bottom 12 with the cell media C dispersing across the bottom 12 and each of the shelves 20. The cap 58 may be mounted to the tubular neck 16 to seal the opening 18. Thereafter, the vessel 10 may be placed in an incubator. For transportation, it is preferred that the vessel 10 be held upright with the cell media C being accumulated in the enclosed volume 22 adjacent to the first end 38. A plurality of the vessels 10 may be stacked during incubation.

To extract the cell media C for exchange or cell harvesting purposes, the vessel 10 may be set upon the first end 38. A pipette, or other extraction device, may be introduced to extract the cell media C from adjacent the first end 38. This permits thorough removal. The pipette may be introduced into the enclosed volume 22 in between the top 14 and the adjacent shelf 20 to access the volume adjacent to the first end 38 for extraction. Under negative pressure, the cell media C may be caused to be drawn through the flow apertures 32b to the volume adjacent the top 14 for extraction therefrom. Alternatively, the cell media C may be caused to be poured through the opening 18. Trypsin, or other disassociation agents, may be utilized to release cells for harvest.

What is claimed is:

1. A vessel for culturing cells comprising:
    a bottom including a base with an upwardly extending wall at least partially bounding the base of the bottom;
    a top including a base with a downwardly extending wall at least partially bounding the base of the top;
    a tubular neck with an opening defined therein; and,
    at least one shelf, wherein, each shelf includes a base with an upwardly extending wall at least partially bounding the base of the shelf,
    wherein,
        the upwardly extending wall of a first shelf adjoins the downwardly extending wall of the top,
        the first shelf being located intermediate the bottom and the top,
        the base of each of the shelves having at least one aperture formed therein, and
    wherein,
        the bottom, the top and the shelves collectively define an enclosed volume for culturing cells, the tubular neck extending from the vessel, the enclosed volume being accessible by the opening in the tubular neck, wherein the at least one shelf includes a second shelf, the second shelf being located intermediate the bottom and the first shelf, the wall of the bottom adjoining the second shelf, wherein the vessel has spaced-apart first and second ends, the tubular neck extending from the second end, a first volume being defined between the top and the first shelf extending a predetermined length from the first end, the predetermined length being less than the spacing between the first and second ends, a second volume being defined between the bottom and the second shelf extending the predetermined length from the first end, the first and second volumes being substantially equal, wherein the opening is aligned to permit pipette access to the first volume in proximity to the first end of the vessel between the top and the first shelf, wherein a flow aperture is formed in each of the shelves in proximity to the first end of the vessel, the first volume being in communication with the flow aperture of the first shelf, the second volume being in communication with the flow aperture of the second shelf, wherein the base of the top having a first portion spaced a first distance from the base of the first shelf, the base of the top having a second portion spaced a second distance from the base of the first shelf, the first distance being greater than the second distance, and, wherein the second portion extends from the first end of the vessel the predetermined length.

2. The vessel of claim 1, wherein the base of the top includes a third portion extending between, and joining, the first and second portions of the base of the top.

3. The vessel of claim 2, wherein the first and second portions of the base of the top are disposed to be generally parallel.

4. The vessel of claim 3, wherein the third portion is generally flat and disposed at an angle relative to a plane defined by the second portion of the base, the angle being in the range of about 10-90 degrees.

5. The vessel of claim 4, wherein the angle is in the range of about 20-40degrees.

6. The vessel of claim 4, wherein the angle is about 30 degrees.

7. The vessel of claim 1, wherein the tubular neck extends from the top.

8. The vessel of claim 1, wherein the top further includes at least one vented opening.

9. The vessel of claim 8, wherein a gas permeable membrane extends across the vented opening.

10. The vessel of claim 1, wherein the opening in the tubular neck is elliptical or semi-circular.

11. The vessel of claim 1, wherein the tubular neck extends along a longitudinal axis, the longitudinal axis being disposed at an angle relative to a plane defined by the base of the first shelf, the angle being in the range of about 0 degrees-90 degrees.

12. The vessel of claim 11, wherein the angle is about 0 degrees.

13. The vessel of claim 11, wherein the angle is about 90 degrees.

14. The vessel of claim 11, wherein the angle is an acute angle.

15. The vessel of claim 1, wherein a gas-transmission aperture is formed in each of the shelves, the gas-transmission apertures of the shelves being in linear registration to define a gas flow channel.

16. The vessel of Channel 15, wherein the gas flow channel extends into proximity to the opening defined in the tubular neck.

17. The vessel of claim 15, wherein the flow aperture for each of the shelves being spaced from the gas-transmission aperture of the respective shelf.

18. The vessel of claim 1, wherein each shelf includes a containment wall extending upwardly from the base, the containment wall defined along at least a portion of an aperture.

19. The vessel of claim 18, wherein the containment wall is bowed along an arcuate longitudinal axis.

20. The vessel of claim 18, wherein the containment wall is angularly disposed relative to the base of the respective shelf.

21. The vessel of claim 18, wherein the containment wall has an arcuate cross-section.

22. The vessel of claim 18, wherein the containment wall includes a non-smooth surface facing away from the respective aperture.

23. The vessel of claim 18, wherein the containment wall terminates at a free edge, the containment wall being hydrophobic along at least the free edge.

24. The vessel of claim 23, wherein the base of the respective shelf having hydrophilic portions spaced from the containment wall.

25. An assembly comprising:
a vessel formed in accordance with claim 1; and,
a cap formed to mount onto the tubular neck.

26. The assembly of claim 25, wherein the cap is vented.

27. The assembly of claim 25, wherein the cap is not vented.

28. The assembly of claim 25, wherein the cap includes a valve for permitting selective access to the enclosed volume.

29. The assembly of claim 25, wherein the cap includes means for connecting one or more tubes.

* * * * *